United States Patent [19]

Margraff

[11] Patent Number: 5,393,896
[45] Date of Patent: Feb. 28, 1995

[54] PROCESS FOR OBTAINING 10-DEACETYLBACCATIN III

[75] Inventor: Rodolphe Margraff, Viry Chatillon, France

[73] Assignee: Rhone-Poulenc Rorer, S.A., Antony, France

[21] Appl. No.: 10,084

[22] Filed: Jan. 27, 1993

[30] Foreign Application Priority Data

Oct. 5, 1992 [FR] France .................. 92 11745

[51] Int. Cl.$^6$ .......................... C07D 305/14
[52] U.S. Cl. ............................... 549/510
[58] Field of Search ............... 568/320; 549/510, 541

[56] References Cited

FOREIGN PATENT DOCUMENTS 0253738 1/1988 European Pat. Off. .
0253739 1/1988 European Pat. Off. .
0336840 10/1989 European Pat. Off. .
0336841 10/1989 European Pat. Off. .
0400971 12/1990 European Pat. Off. .
0428376 5/1991 European Pat. Off. .

Primary Examiner—José G. Dees
Assistant Examiner—Joseph M. Conrad, III
Attorney, Agent, or Firm—Morgan & Finnegan

[57] ABSTRACT

This invention relates to a process for obtaining 10-deacetylbaccatin III from various parts of yew (Taxus sp.) by extraction with a suitable organic solvent of the aqueous solution obtained after treating the appropriate part of yew with water, followed by selective crystallization of 10-deacetylbaccatin III.

32 Claims, No Drawings

PROCESS FOR OBTAINING 10-DEACETYLBACCATIN III

FIELD OF THE INVENTION

The present invention relates to a process for obtaining intermediates used for the preparation, using semisynthetic processes, of taxol, of Taxotère or of their analogues from various parts of plants containing these intermediates.

More particularly, the invention relates to the selective preparation of 10-deacetylbaccatin III from the bark, the trunk, the roots or the foliage of various species of yew.

BACKGROUND OF THE INVENTION

Taxol and Taxotère and their analogues of general formula:

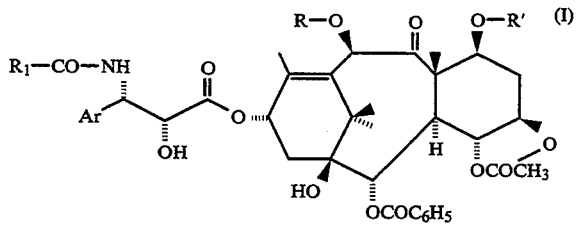

which exhibit remarkable anticancer and antileukaemia properties, constitute remarkable chemotherapeutic agents for the treatment of a number of cancers such as, for example, cancers of the breast, of the prostate, of the colon, of the stomach, of the kidney, of the testicles and more especially cancer of the ovary.

In particular, in the general formula (I), Ar may denote an optionally substituted phenyl radical, R may denote a hydrogen atom or an acetyl radical or an N-substituted carbamoyl radical, R' denotes a hydrogen atom or an N-substituted carbamoyl radical and $R_1$ may denote a phenyl radical or a radical $R_2$—O— in which $R_2$ denotes an alkyl, alkenyl, alkynyl, cycloalkyl, cycloalkenyl, bicycloalkyl, phenyl or heterocyclyl radical.

Taxol corresponds to the product of general formula (I) in which Ar and $R_1$ denote a phenyl radical and R denotes an acetyl radical and R' denotes a hydrogen atom, and Taxotère corresponds to the product of general formula (I) in which Ar denotes a phenyl radical, R and R' denote a hydrogen atom and $R_1$ denotes a t-butoxy radical.

Taxol, which exists in the natural state in various species of yew, in which it is present in small quantities, is difficult to isolate without effecting the total destruction of the plant. For example, taxol can be isolated by the method of C. H. O. Huang et al. J. Natl. Prod. 49,665 (1986), which consists in treating ground bark of Taxus brevifolia with methanol, concentrating the extract, extracting the concentrate with dichloromethane, reconcentrating, dispersing the residue in a hexane-acetone mixture (1—1 by volume), purifying the soluble part by chromatography on a Florisil column to obtain crude taxol, which is purified by successive recrystallizations from methanol-water and hexane-acetone mixtures and then chromatography and further crystallization. The quantities of taxol which are thus extracted can represent from 0.005 to 0.017% of the part of the plant which is used.

Taxotère, which does not exist in the natural state, can be prepared by partial synthesis from 10-deacetylbaccatin III of formula:

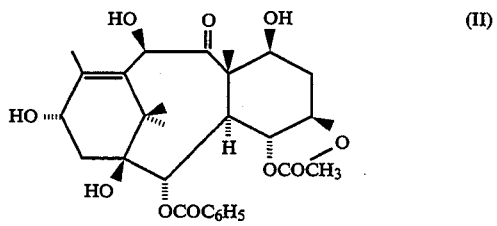

by processes which are described, for example, in U.S. Pat. Nos. 4,814,470 or 4,924,012 or in international application PCT WO 92/09589.

Taxol can also be prepared by processes which involve the use of 10-deacetylbaccatin III or by going through the Taxotère intermediate under the conditions described in U.S. Pat. No. 4,857,653 or by esterification of baccatin III under the conditions described in European Patents EP 400,971 or EP 428,376 or by esterification of 10-deacetylbaccatin III and acetylation under the conditions described in U.S Pat. No. 4,924,011.

The different varieties of yew (Taxus baccata, Taxus brevifolia, Taxus canadensis, Taxus cuspidata, Taxus floridana, Taxus media, Taxus wallichiana) contain taxane derivatives, the main ones of which are essentially taxol and 10-deacetylbaccatin III, the other derivatives being more particularly cephalomannin, 10-deacetylcephalomannin or baccatin III, optionally bonded to sugars.

Whereas taxol is present chiefly in the trunk and the bark, 10-deacetylbaccatin III is present essentially in the foliage. Furthermore, the content of 10-deacetylbaccatin III in the foliage is generally much higher than that of taxol, whether the latter be present in the bark, the trunk or in the foliage.

As a result, it is particularly important to be able to have access to 10-deacetylbaccatin III, which is essential for the preparation of much larger quantities of taxol than by direct extraction from yew, and for the preparation of Taxotère.

Extraction of 10-deacetylbaccatin III from yew foliage does not result in a total destruction of the plant, whose foliage can be employed again after each growth cycle.

In general, the known methods for extracting taxane derivatives present in the various parts of the yew (bark, trunk, roots, foliage etc.) require the use of long and costly chromatographic techniques which do not permit a complete and quantitative separation of the taxane derivatives initially present in the plant.

10-Deacetylbaccatin III can be obtained, in yields of about 300 mg per kg of foliage (Taxus baccata) by a process which uses wet grinding of the needles in ethanol, extraction with an organic solvent such as methylene chloride and successive chromatographies by the process which is described in U.S. Pat. No. 4,814,470.

The various constituents derived from taxane which are present in the various parts of the yew can also be separated by methods using reverse-liquid phase chromatography which are described in particular in international application PCT WO 92/07842. These processes consist essentially in treating the crude yew extracts by reverse liquid phase chromatography on an adsorbent on which the taxane derivatives are immobilized, in eluting the taxane derivatives and in isolating them. According to this process it is possible to isolate 200 mg of 10-deacetylbaccatin III from 1 kg of ground and dried foliage.

DESCRIPTION OF THE INVENTION

It has now been found, and this is what forms the subject of the present invention, that 10-deacetylbaccatin III can be extracted very selectively and in an excellent yield from various parts of yew, and more particularly the foliage, by a simple process which does not involve chromatographic techniques. For example, it is possible to extract approximately 800 mg of 10-deacetylbaccatin III per kg of yew foliage (*Taxus baccata*).

More particularly, the process according to the invention consists 1) in treating the ground parts of yew (Taxus sp.) with water,
2) in separating the aqueous solution containing 10-deacetylbaccatin III from the vegetable matter in suspension,
3) in extracting 10-deacetylbaccatin III from the aqueous solution with an organic solvent,
4) in separating the organic extract containing 10-deacetylbaccatin III from the aqueous phase,
5) in removing the organic solvent from the organic extract thus separated,
6) in selectively crystallizing 10-deacetylbaccatin III from the residue thus obtained in an organic solvent,
7) in isolating 10-deacetylbaccatin III in purified form.

The process according to the invention can be carried out on any appropriate part of yew, such as the bark, the trunk, the roots or the foliage. The yew employed for carrying out the process according to the invention preferably belongs to the *Taxus baccata, Taxus brevifolia, Taxus canadensis, Taxus cuspidata, Taxus floridana, Taxus media* or *Taxus wallichiana* variety. It is particularly advantageous to employ yew foliage (*Taxus baccata, Taxus brevifolia*) which is generally richer in 10-deacetylbaccatin III. The fragments employed may vary from 0.5 to a few millimeters in size. For reasons of convenience it may be advantageous to employ fragments whose average size is less than 1 mm. The ground and optionally dried parts of yew can be obtained by grinding and optionally drying operations which, optionally, precede or follow the operations of freezing and thawing of the fresh parts of the plant or are interposed between the operations of freezing and thawing of the fresh parts of the plant.

The water treatment of the ground parts of yew is performed by techniques which are known to a person skilled in the art. In particular, aqueous solution containing 10-deacetylbaccatin III is generally obtained by stirring, at a temperature of between 20° and 65° C., ground parts of yew in water for 30 minutes to 2 hours. The quantity of water which is employed may vary within wide limits, but it is suitable to employ a quantity of water of 2 to 10 liters, calculated per kg of ground and dried plant part, and preferably approximately 5 liters of water per kg of plant part to be treated. It may be advantageous to employ demineralized water for performing this treatment and to operate under ultrasound.

In order to improve the yield it may be advantageous to perform a number of water treatments on the vegetable matter in order to obtain aqueous solutions from which 10-deacetylbaccatin III is extracted under the conditions described below.

The aqueous solution obtained, containing 10-deacetylbaccatin-III, is separated from the vegetable matter by conventional techniques such as filtration, centrifuging or sedimentation. The resulting aqueous solution is optionally cooled and then 10-deacetylbaccatin III is extracted, one or more times, with an organic solvent. Organic solvents which are particularly suitable are chosen from ethers such as methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether or ethyl n-hexyl ether, and aliphatic esters such as ethyl acetate, propyl acetate, isopropyl acetate, n-butyl acetate, t-butyl acetate, methyl t-butylacetate, t-butyl propionate or t-amyl acetate. Methyl t-butyl ether, ethyl t-butyl ether, ethyl acetate and n-butyl acetate are of very particular interest.

The extraction with an organic solvent is generally performed on an aqueous solution whose pH is lower than 7 and preferably lower than 6.

The organic extracts containing 10-deacetylbaccatin III are separated from the aqueous phase by the application of conventional techniques such as sedimentation.

The organic extracts are optionally washed by means of an aqueous solution of a weak base (for example aqueous solution of sodium carbonate) and/or water. After drying, the organic solvent of the extract is removed by conventional methods and in particular by distillation, optionally at reduced pressure, to give a generally solid residue from which 10-deacetylbaccatin III is isolated.

Selective crystallization of 10-deacetylbaccatin III is performed from a solution of the residue obtained in an organic solvent or in a mixture of organic solvents. Solvents which make it possible to crystallize 10-deacetylbaccatin III selectively and which can advantageously be employed are nitriles such as acetonitrile or isobutyronitrile optionally mixed with an aliphatic alcohol such as methanol, ethanol, propanol, isopropanol or n-butanol, or an aliphatic ester such as ethyl acetate, n-butyl acetate or t-butyl acetate or an aliphatic ketone such as acetone, methyl ethyl ketone, methyl propyl ketone, methyl n-butyl ketone or methyl isobutyl ketone. It is particularly advantageous to perform the selective crystallization from acetonitrile, optionally in the presence of ethanol and/or ethyl or n-butyl acetate and/or acetone.

The 10-deacetylbaccatin III which precipitates can be separated off by filtration, sedimentation or centrifuging.

The process according to the invention makes it possible to obtain 10-deacetylbaccatin III practically pure in the yields which are generally greatly superior to those obtained by the use of the previously known processes. The process according to the invention makes it possible to extract virtually quantitatively all the 10-deacetylbaccatin III contained in the parts of the plant which are employed, and in particular the foliage.

The 10-deacetylbaccatin III obtained by the extraction process of the present invention can be employed for preparing taxol or Taxotère or their derivatives under the conditions which are described more particularly in patents EP 0,253,738, EP 0,253,739, EP 0,336,841, EP 0,336,840, WO 92/09589, EP 0,400,971 and EP 0,428,376.

EXAMPLES

The following examples illustrate the process according to the invention.

Example 1

To 2.5 liters of demineralized water heated to 50° C. are added 500 g of ground and dried yew (*Taxus baccata*) leaves whose mean particle size is smaller than 1 mm and whose 10-deacetylbaccatin III content, determined by high performance liquid chromatography (HPLC) is 0.08% (that is 400 mg of 10-deacetylbaccatin III in 500 g of foliage). The mixture is stirred for 1 hour at 50° C. and is then filtered.

The filtrate (1.8 liters), whose pH is 5.4, is extracted with 3 times 0.9 liters of ethyl acetate. The combined organic phases (2.7 liters) are washed with 2 1-liter portions of a 0.1M sodium carbonate solution and then twice with 1-liter portions of demineralized water and are finally dried over sodium sulphate. After filtration and concentration to dryness, a solid (3.2 g) is obtained, which is taken up with 9 cm$^3$ of acetonitrile at a temperature close to 70° C. After cooling overnight at a temperature of +4° C. the precipitate is separated by filtration. In this way, after drying, 245 mg of crystals are obtained containing, according to HPLC analysis, 75% of pure 10-deacetylbaccatin III, that is 183 mg. According to HPLC analysis, the mother liquors contain 40 mg of 10-deacetylbaccatin III.

The vegetable mass, which has retained 0.7 liters of water, is extracted twice under the conditions described above. The combined aqueous filtrates are treated as above. This yields 2.5 g of a solid product which is taken up in 5 cm$^3$ of acetonitrile at a temperature close to 70° C. After cooling overnight at a temperature close to +4° C., 169 mg of crystals containing, according to HPLC analysis, 75% of pure 10-deacetylbaccatin III, that is 127 mg, are separated off by filtration. According to HPLC analysis, the mother liquors contain 47 mg of 10-deacetylbaccatin III.

The total quantity of 10-deacetylbaccatin III extracted with water is 183+40+127+47=397 mg.

The yield is practically quantitative.

Example 2

3 liters of demineralized water are heated to 50° C. and then 500 g of ground and dried yew leaves are added, whose mean particle diameter is 1 mm and whose 10-deacetylbaccatin III content, determined by high performance liquid chromatography (HPLC) is 0.08% (that is 400 mg of 10-deacetylbaccatin III in 500 g of foliage). The mixture is stirred for 1 hour at 50° C. and is then filtered. The filtrate (1.97 liters), whose pH is 5.15, is adjusted to pH=4.6 by addition of concentrated hydrochloric acid and is then filtered on an asbestos card membrane in a Seitz filter. 1.8 liters of filtrate are collected.

300 cm$^3$ of filtrate are extracted with 2 times 150 cm$^3$ then 4 times 60 cm$^3$ of methyl tert-butyl ether (MTBE). The combined and concentrated extracts yield 620 mg of solids, which are taken up with 3 cm$^3$ of acetonitrile at 70° C.

After cooling overnight at +4° C., 28 mg of crystalline 10-deacetylbaccatin III are separated off by filtration, the content of which, determined by HPLC, is 90%. The mother liquors contain 12.8 mg of 10-deacetylbaccatin III (determination by HPLC).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

I claim:

1. A process for obtaining 10-deacetylbaccatin III from various parts of yew (Taxus sp.) comprising:
    1) treating ground parts of yew with water to obtain an aqueous suspension,
    2) separating an aqueous solution containing 10-deacetylbaccatin III from vegetable matter in the aqueous suspension,
    3) extracting 10-deacetylbaccatin III from the aqueous solution with an organic solvent,
    4) separating an organic extract containing 10-deacetylbaccatin III from the aqueous phase,
    5) removing the organic solvent from the organic extract thus separated to obtain a residue,
    6) selectively crystallizing 10-deacetylbaccatin III from the residue thus obtained in an organic solvent,
    7) isolating 10-deacetylbaccatin III in purified form.

2. A process according to claim 1, wherein the ground dried parts of yew are stirred with water at a temperature of between 20° and 65° C.

3. A process according to claim 2, wherein the ground parts of yew are dried.

4. A process according to claim 1, wherein the aqueous solution containing 10-deacetylbaccatin III is separated from the vegetable matter in suspension by filtration, centrifugation, or by sedimentation.

5. A process according to claim 1, wherein the aqueous solution containing 10-deacetylbaccatin III is extracted with an organic solvent selected from the group consisting of ethers and aliphatic esters.

6. A process according to claim 5, wherein the organic solvent is selected from the group consisting of methyl t-butyl ether, ethyl t-butyl ether, methyl n-butyl ether, methyl n-amyl ether, ethyl t-amyl ether, t-butyl isopropyl ether, ethyl isobutyl ether, t-butyl n-propyl ether, ethyl n-hexyl ether, ethyl acetate, propyl acetate, isopropyl acetate, n-butyl acetate, t-butyl acetate, methyl t-butylacetate, t-butyl propionate, and t-amyl acetate.

7. A process according to claim 5, wherein the solvent is selected from the group consisting of methyl t-butyl ether, ethyl t-butyl ether, ethyl acetate, and n-butyl acetate.

8. A process according to claim 6, wherein the operation is carried out with an aqueous solution whose pH is lower then 7.

9. A process according to claim 7, wherein the pH of the aqueous solution is lower than 6.

10. A process according to claim 1, wherein the organic extract containing 10-deacetylbaccatin III is separated from the aqueous solution by gravity separation.

11. A process according to claim 1, wherein the solvent is removed from the organic extract containing 10-deacetylbaccatin III by distillation.

12. A process according to claim 11, wherein the organic extract is washed with an aqueous solution of a weak base and/or water prior to removal of the organic solvent.

13. A process according to claim 11, wherein the distillation is performed at reduced pressure.

14. A process according to claim 1, wherein 10-deacetylbaccatin III is selectively crystallized from the residue obtained after the removal of the solvent, in an organic solvent or in a mixture of organic solvents.

15. A process according to claim 14, wherein the solvent is aliphatic nitriles or aliphatic nitriles mixed with an aliphatic alcohol or an aliphatic ester or an aliphatic ketone.

16. A process according to claim 15, wherein the nitriles are acetonitrile or propionitrile.

17. A process according to claim 15, wherein the aliphatic alcohol is methanol, ethanol, propanol, isopropanol, or n-butanol.

18. A process according to claim 15, wherein the aliphatic ester is ethyl acetate, isopropyl acetate, n-butyl acetate, or t-butyl acetate.

19. A process according to claim 15, wherein the aliphatic ketone is acetone, methyl ethyl ketone, methyl propyl ketone, methyl n-butyl ketone, or methyl isobutyl ketone.

20. A process according to claim 15, wherein the selective crystallization is performed in acetonitrile optionally combined with ethanol and/or ethyl or n-butyl acetate and/or acetone.

21. A process according to claim 1, wherein 10-deacetylbaccatin III in purified form is isolated by filtration, sedimentation, or centrifuging.

22. A process according to claim 1, wherein 10-deacetylbaccatin III is extracted from the bark, the trunk, the roots, or the foliage of yew.

23. A process according to claim 1, wherein 10-deacetylbaccatin III is extracted from yew foliage.

24. A process according to claim 1, wherein the yew belongs to the *Taxus baccata, Taxus brevifolia, Taxus canadensis, Taxus cuspidata, Taxus floridana, Taxus media*, or *Taxus wallichiana* variety.

25. A process according to any of claims 2 or 3, wherein the ground or the ground dried parts of yew are obtained by grinding or grinding and drying operations which, optionally, precede or follow the operations of freezing and thawing of the fresh parts of the plant or are interposed between the operations of freezing and thawing of the fresh parts of the plant.

26. A process according to any of claims 2 or 3, wherein from 2 to 10 liters of water are employed per kg of ground or ground and dried plant part.

27. A process according to either of claims 2, or 3, wherein demineralized water is employed.

28. A process according to either of claims 2, or 3, wherein the operation is carried out under ultrasound.

29. A process according to claim 25, wherein demineralized water is used.

30. A process according to claim 26, wherein demineralized water is used.

31. A process according to claim 25, wherein the operation is carried out under ultrasound.

32. A process according to claim 26, wherein the operation is carried out under ultrasound.

* * * * *